US005328693A

United States Patent [19]

Horstmann et al.

[11] Patent Number: 5,328,693

[45] Date of Patent: Jul. 12, 1994

[54] N-ALLYL-LACTAMS AS CRYSTALLIZATION INHIBITORS

[75] Inventors: Heinz-Otto Horstmann, Bergisch Gladbach; Klaus Wangermann, Krefeld, both of Fed. Rep. of Germany

[73] Assignee: Bayer Aktiengesellschaft, Leverkusen, Fed. Rep. of Germany

[21] Appl. No.: 893,968

[22] Filed: Jun. 4, 1992

Related U.S. Application Data

[63] Continuation of Ser. No. 688,181, Apr. 19, 1991, abandoned.

[30] Foreign Application Priority Data

Apr. 27, 1990 [DE] Fed. Rep. of Germany ....... 4013523

[51] Int. Cl.[5] ...................... A01N 25/00; A01N 43/64

[52] U.S. Cl. .................................. 424/405; 514/383; 514/212; 514/350; 514/424

[58] Field of Search ................. 424/47, 404, 405, 407; 514/383

[56] References Cited

FOREIGN PATENT DOCUMENTS 0077078 4/1983 European Pat. Off. ..... A01N 43/36
0095242 11/1983 European Pat. Off. .
0391168 10/1990 European Pat. Off. .
0391171 10/1990 European Pat. Off. .
8800184 1/1988 PCT Int'l Appl. ...... C07D 207/267

OTHER PUBLICATIONS

Chemical Abstracts, vol. 84, No. 23 Jun. 7, 1976, p. 118, par. 160605p. Columbus, Ohio, US: & JP A 74 092 231 (Mitsubishi Petrochemical Co.) Mar. 9, 1974.

*Primary Examiner*—Thurman K. Page
*Assistant Examiner*—Neil Levy
*Attorney, Agent, or Firm*—Sprung Horn Kramer & Woods

[57] ABSTRACT

Crystallization of active material in spraying of an aqueous solution of certain specified fungicides is retarded by incorporation therein of an N-alkyl-lactam of the formula

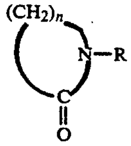

(I)

in which

R represents alkyl having 6 to 18 carbon atoms and
n represents the numbers 3, 4 or 5.

8 Claims, 1 Drawing Sheet

N-ALLYL-LACTAMS AS CRYSTALLIZATION INHIBITORS

This application is a continuation, of application Ser. No. 688,181, filed Apr. 19, 1991, now abandoned.

The present invention relates to the new use of N-alkyl-lactams for the prevention of crystallization during the application of aqueous spray liquors based on specific fungicidal active compounds.

In spray equipment which is customarily used for the application of aqueous formulations of plant treatment agents, several filters and nozzles are present. Thus, for example, suction filters are situated between suction component and tank pump and in addition pressure filters which are located in the pressure region after the pump. In addition, nozzle filters may also be present which are situated directly upstream of the spray nozzles. All these filters and also the nozzles can block more or less easily as a result of crystallizing active compound during the application of aqueous spray liquors based on solid active compounds.

Figure 1:
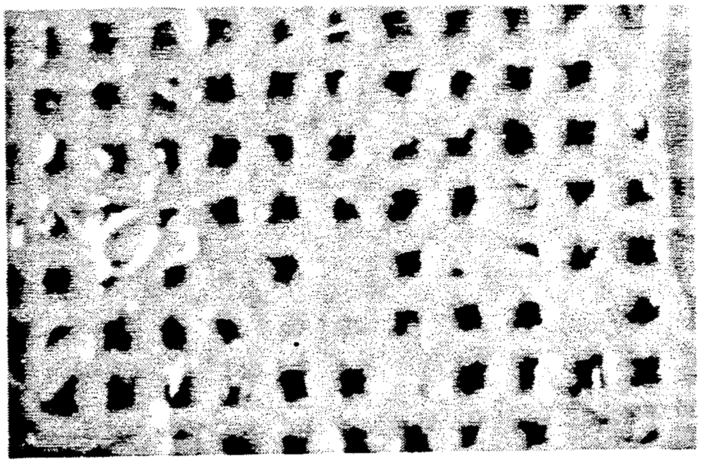
FIG. 1 shows crystal formation.

It is already known that the azole derivatives mentioned below are fungicidally active and can be applied in the form of aqueous spray liquors to plants and/or their environment: 1-(2-chlorophenyl)-2-(1-chloro-cycloprop-1-yl)-3-(1,2,4-triazol-1-yl)-propan-2-ol, 1-(4-fluorophenyl)-1-(2-fluorophenyl)-2-(1,2,4-triazol-1-yl)-ethan-1-ol, 1-(1,2,4-triazol-1-yl)-2-(2,4-dichlorophenyl)-hexan-2-ol, 1-[bis-(4-fluorophenyl)-methyl-silyl]-1H-(1,2,4-triazole), 1-(4-chlorophenyl)-2-(1,2,4-triazol-1-yl)-4,4-dimethylpent-1-en-3-ol, 1-(2,4-dichlorophenyl)-2-(1,2,4-triazol-1-yl)-4,4-dimethyl-pent-1-en-3-ol, 1-(4-chlorophenyl)-1-(1-cyclopropyl-ethyl)-2-(1,2,4-triazol-1-yl)-ethan-1-ol and 1-(4-chlorophenyl)-3-phenyl-3-cyano-4-(1,2,4-triazol-1-yl)-butane (compare EP-OS (European Published Specification) 0,297,345, EP-OS (European Published Specification) 0,015,756, U.S. Pat. No. 4,551,469, EP-OS (European Published Specification) 0,068,8137 DE-OS (German Published Specification) 2,838,847, DE-OS (German Published Specification) 3,010,560, DE-OS (German Published Specification) 3,406,993 and DE-OS (German Published Specification) 2,821,971).

Surface-active substances, such as, for example, alkylaryl polyglycol ethers can be employed for the preparation of spray liquors of this type. However, a disadvantage in the use of these conventional formulations is that the active compounds tend to crystallize and both filters and nozzles of the spray equipment can block.

It has now been found that N-alkyl-lactams of the formula

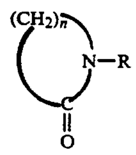

(I)

in which

R represents alkyl having 6 to 18 carbon atoms, and n represents the numbers 3, 4 or 5, can be used during application of aqueous spray liquors which contain A) 1-(2-chlorophenyl)-2-(1-chloro-cycloprop-1-yl)-3-(1,2,4-triazol-1-yl)-propan-2-ol of the formula

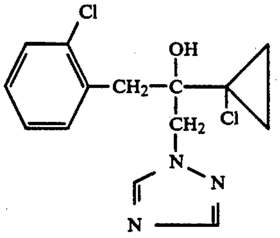

(II)

and/or 1-(4-fluorophenyl)-1-(2-fluorophenyl)-2-(1,2,4-triazol-1-yl)-ethan-1-ol of the formula

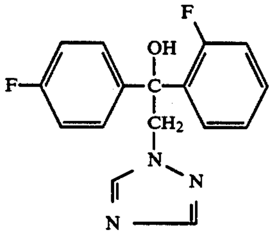

(III)

and/or 1-(1,2,4-triazol-1-yl)-2-(2,4-dichlorophenyl)-hexan-2-ol of the formula

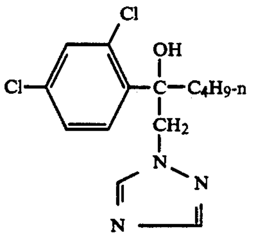

(IV)

and/or

1-[bis-(4-fluorophenyl)-methyl-silyl]-1H-(1,2,4-triazole) of the formula

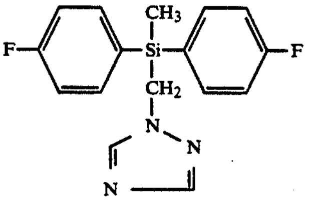

(V)

and/or

1-)4-chlorophenyl)-2-(1,2,4-triazol-1-yl)-4,4-dimethyl-pent-1-en-3-ol of the formula

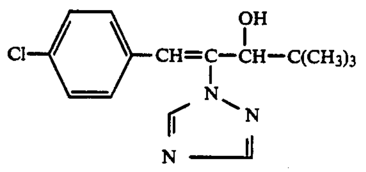
(VI)

and/or 1-(2,4-dichlorophenyl)-2-(1,2,4-triazol-1-yl)-4,4-dimethyl-pent-1-en-3-ol of the formula

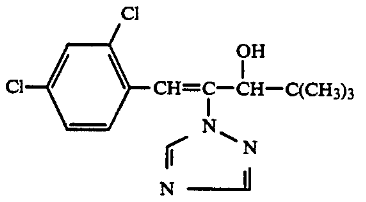
(VII)

and/or 1-(4-chlorophenyl)-1-(1-cyclopropyl-ethyl )-2-(1,2,4-triazol-1-yl)-ethan-1-ol of the formula

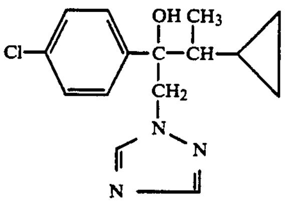
(VIII)

and/or 1-(4-chlorophenyl)-3-phenyl-3-cyano-4-(1,2,4-triazol-1-yl)-butane of the formula

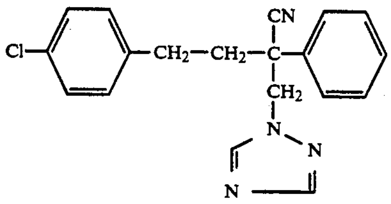
(IX)

and

B) if desired, one or more further active compounds and additives, for the prevention of crystallization of active compounds of the formulae (II) to (IX).

It is to be indicated as extremely surprising that the crystallization tendency of active compounds of the formulae (II) to (IX) in the spray liquor is greatly reduced by the use according to the invention of N-alkyl-lactams of the formula (I) . Above all, it was not to be expected that N-alkyl-lactams of the formula (I) would be substantially better suited than other comparably acting substances for the purpose indicated.

The use of N-alkyl-lactams of the formula (I) in aqueous formulations based on the fungicidal active compounds of the formulae (II) to (IX) has a number of advantages. Thus, the N-alkyl-lactams of the formula (I) are substances which can be handled without problems and are also available in relatively large amounts. In addition, during spraying of aqueous formulations which contain active compounds of the formulae (II) to (IX), the use of the substances of the formula (I) prevents both the filters and the nozzles of the spray equipment from blocking. It is also advantageous that N-alkyl-lactams of the formula (I) have no undesired side effects in plant protection.

Formula (I) provides a general definition of the N-alkyl-lactams which can be used according to the invention. Substances of the formula (I) which can preferably be used are those in which R represents alkyl having 8 to 14 carbon atoms and n represents the numbers 3, 4 or 5.

Those substances of the formula (I) can particularly preferably be used in which R represents alkyl having 8, 10 or 12 carbon atoms and n represents the numbers 3, 4 or 5.

Examples of N-alkyl-lactams of the formula (I) which may be mentioned are:

N-dodecyl-caprolactam
N-decyl-caprolactam
N-octyl-caprolactam
N-dodecyl-pyrrolidone
N-decyl-pyrrolidone
N-octyl-pyrrolidone
N-dodecyl-valerolactam
N-decyl-valerolactam
N-octyl-valerolactam.

The N-alkyl-lactams of the formula (I) are already known (compare J. Org. Chem. 18, 1087 (1953); Ann. Chem. 596, 203 (1955); J. Amer. Chem. Soc. 69, 715 (1947); DE-AS (German Published Specification) 1,160,268; EP-OS (European Published Specification) 0,077,078 and WO 88/00 184).

The active compounds of the formulae (II) to (IX) and their use for combating phytopathogenic fungi are also known (compare EP-OS (European Published Specification 0,297,345, EP-OS (European Published Specification) 0,015,756, U.S. Pat. No. 4,551,469, EP-OS (European Published Specification 0,068,813, DE-OS (German Published Specification 2,838,847, DE-OS (German Published Specification) 3,010,560, DE-OS (German Published Specification) 3,406,993 and DE-OS (German Published Specification) 2,821,971). The active compounds can be employed in customary formulations. Preferably, they are applied in the form of aqueous spray liquors.

In addition to the active compounds of the formulae (II) to (IX), one or more other active compounds can also be present in the spray liquors which can be used according to the invention. Those which are preferably suitable in this case are compounds having fungicidal properties. Examples of active compounds of this type which can additionally be used and which may be mentioned are: 1-(4-chlorophenoxy)-3,3-dimethyl-(1,2,4-triazol-1-yl)-butan-2-one (triadimefon), 1-(4-phenyl-phenoxy)-3,3-dimethyl-(1,2,4-triazol-1-yl)-butan-2-ol (bitertanol), N,N-dimethyl-N'-phenyl-(N'-fluorodichloromethylthio)-sulphamide (dichlofluanid), N,N-dimethyl-(N'-fluorodichloromethylthio)-N'-(4-methyl-phenyl)-sulphamide (tolylfluanid) N-trichloromethyl-mercapto-4-cyclohexene-1,2-dicarboxamide (captan), N-(1,1,2,2-tetrachloroethyl-sulphenyl)-cis-4-cyclohex-en-1,2-dicarboxamide (captafol), N-trichloromethylthio-phthalimide (folpet), N-dodecyl-guanidine acetate (dodine), tetrachloro-isophthalo-dinitrile (chlorothalonil), 4,5,6,7-tetrachlorophthalide, zinc-ethylene bis-dithiocarbamate (zineb), manganese-ethylene bis-dithiocarbamate (maneb), zinc-ethylenebis-dithiocarbamate/manganese-ethylenebisdithiocarbamate (mancozeb), zinc-propylene 1,2-bis-dithiocarbamate (propineb), 1-[3-(4-(1,1-dimethylethyl)-phenyl)-2-methylpropyl]-piperidine (fenpropidin), N-tridecyl-2,6-dimethyl-morpholine (tridemorph), N-dodecyl-2,6-dimethyl-morpholine (aldimorph) 2-[2-(2,4-dichlorophenyl)-2-(2-propenyloxy)-ethyl]-imidazole (imazalil), N-[2-(2,4,6-trichlorophenoxy)-ethyl]-N-propyl-1H-imidazole (prochloraz), 1,2-dimethyl-cyclopropane-1,2-dicarboxylic acid-3,5-dichlorophenylimide (procymidone), 2-methoxycarbamoyl-benzimidazole (carbendazim), 1-(butylcarbamoyl)-2-benzimidazolmethyl carbamate (benomyl), 2,4-dichloro-6-(2'-chlorophenylamino)-1,3,4-triazine (anilazine), bis-(8-guanidine-O-octyl)-amine triacetate (guazatine), 1-(4-chlorobenzyl)-1-cyclopentyl-3-phenyl-urea (pencycuron).

Suitable additives which can be present in the spray liquors which can be used according to the invention are surface-active substances, organic diluents, low-temperature stabilizers and adhesives.

Possible surface-active substances in this case are non-ionic and anionic emulsifiers, such as polyoxyethylene fatty acid esters, polyoxyethylene fatty alcohol ethers, alkylaryl polyglycol ethers, alkylsulphonates, alkyl sulphates and aryl sulphonates. The emulsifiers can be employed individually or, alternatively, in a mixture. Those which may preferably be mentioned are polyoxyethylene sorbitan monolaurate having on average 20 oxyethylene units per molecule, polyoxyethylene sorbitan monopalmitate having on average 20 oxyethylene units per molecule, polyoxyethylene sorbitan monostearate having on average 20 oxyethylene units per molecule, sorbitan monolaurate, sorbitan monopalmitate, sorbitan monostearate, polyoxyethylene oleyl ether having on average 10 oxyethylene units per molecule, polyoxyethylene oleyl ether having on average 20 oxyethylene units per molecule, bis-[α-methyl-(4-methyl-benzyl)]-phenyl polyglycol ether having on average 27 oxyethylene units per molecule, bis-[α-methyl-(4-n-dodecyl)]-phenyl polyglycol ether having on average 27 oxyethylene units per molecule, bis-(4-methyl-benzyl)-phenyl polyglycol ether having on average 27 oxyethylene units per molecule, bis-(4-n-dodecyl-benzyl)-phenyl polyglycol ether having on average 27 oxyethylene units per molecule, tris-[α-methyl-(4-methyl-benzyl)]-phenylpolyglycol ether having on average 17 oxyethylene units per molecule, bis-(α-methyl-benzyl)-phenyl polyglycol ether having on average 17 oxyethylene units per molecule, tris-(α-methyl-benzyl)-phenyl polyglycol ether having on average 17 oxyethylene units per molecule, bis-(α-methyl-benzyl)-phenyl polyglycol ether having on average 27 oxyethylene units per molecule, tris-(α-methyl-benzyl)-phenyl polyglycol ether having on average 27 oxyethylene units per molecule, bis-(α-methyl-benzyl)-phenyl polyglycol ether having on average 3 oxyethylene units per molecule, tris-(α-methyl-benzyl)-phenyl polyglycol ether having on average 3 oxyethylene units per molecule, nonylphenol polyglycol ether having on average 15 oxyethylene units per molecule, nonylphenol diglycol ether having on average 2 oxyethylene units per molecule, n-dodecyl sodium sulphonate, sodium lauryl sulphate, 4-(n-nonyl)-phenyl-sulphonic acid sodium salt, 4-(tetrapropylene)-phenyl-sulphonic acid sodium salt, 4-(i-dodecyl)-phenyl-sulphonic acid ammonium salt, 4-(i-dodecyl)-phenyl-sulphonic acid calcium salt, 4-(n-dodecyl)-phenyl-sulphonic acid (2-hydroxyethyl)-ammonium salt, 4-(n-dodecyl)-phenyl-sulphonic acid -bis(2-hydroxyethyl)-ammonium salt, 4-(n-dodecyl)-phenyl-sulphonic acid -tris -(2-hydroxyethyl)-ammonium salt, 4-(n-dodecyl)-phenyl-sulphonic acid calcium salt.

The emulsifiers from the alkylaryl polyglycol ether group used in practice are in general mixtures of several compounds. In particular, in this case they are mixtures of substances which differ by the degree of substitution on the phenyl ring connected to the oxyethylene unit and the number of oxyethylene units. As a result, fractional numbers are also calculated as average values for the number of substituents on the phenyl ring. For example, substances may be mentioned for which the following average compositions result:

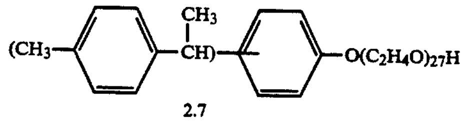

2.7

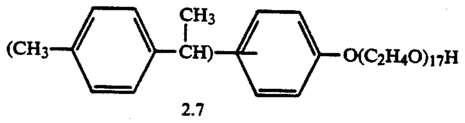

2.7

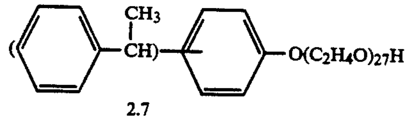

2.7

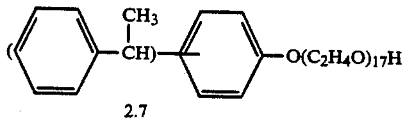

2.7

Organic diluents which can be present in the spray liquors which can be used according to the invention are all polar and non-polar organic solvents-which can customarily be employed for purposes of this type. Those which are preferred are ketones, such as methyl isobutyl ketone and cyclohexanone, in addition amides, such as dimethylformamide and furthermore cyclic compounds, such as N-methyl-pyrrolidone and buyrolactone, and moreover strongly polar solvents, such as dimethyl sulphoxide, and in addition aromatic hydrocarbons, such as xylene, moreover esters, such as propylene glycol monomethyl ether acetate, dibutyl adipate, hexyl acetate, heptyl acetate, tri-n-butyl citrate and di-n-butyl phthalate, and furthermore alcohols, such as ethanol, n-and i-propanol, n- and i-butanol, n- and i-amyl alcohol, benzyl alcohol and 1-methoxypropan-2-ol.

Low-temperature stabilizers which can be present in the spray liquors which can be used according to the invention are all substances customarily suitable for this purpose. Those which are preferred are urea, glycerol and propylene glycol.

Adhesives which can be employed in the spray liquors which can be used according to the invention are all substances which are customarily suitable for this purpose. Those which are preferred are adhesives such as carboxymethyl cellulose, natural and synthetic pulverulent, granular or latex-like polymers, such as gum arabic, polyvinyl alcohol, polyvinyl acetate, and natural phospholipids, such as cephalins and lecithins, and also synthetic phospholipids. Other additives can be mineral and vegetable oils.

Otherwise, water is in each case present in the spray liquors which can be used according to the invention.

In the case of the use of N-alkyl-lactams of the formula (I) according to the invention, one or, alternatively, several of these N-alkyl-lactams can be employed in the spray liquors.

The active compound concentrations can be varied within a specific range in the spray liquors which can be used according to the invention. In general, the active compound concentrations are between 0.0001 and 3 per cent by weight, preferably between 0.001 and 2 per cent by weight.

The ratio of active compound to N-alkyl-lactams of the formula (I) can also be varied within a specific range. In general, the weight ratio of active compound from the group (A) to N-alkyl-lactams of the formula (I) is between 1:0.2 and 1:6, preferably between 1:0.6 and 1:4.

The amounts of other active compounds or additives can be varied within a relatively wide range in the spray liquors which can be used according to the invention. They are of the order of magnitude which is customarily the case in aqueous spray liquors of this type.

The spray liquors which can be used according to the invention are prepared by customary methods. In general, a procedure is used in which a concentrate is first prepared by adding together the required components in any desired sequence at temperatures between 10° and 30° C. and homogeneously mixing and if desired filtering the resulting mixture. To prepare the ready-to-use spray liquors, the concentrated formulation is mixed, if desired with stirring and/or pumping, with the amount of water desired in each case such that the formulation is distributed in water uniformly and in finely dispersed form.

It is also possible to add one or more N-alkyl-lactams of the formula (I) when the concentrate is diluted with water to give the ready-to-use spray liquor.

Both for the preparation of the concentrated formulations and for the preparation and application of the spray liquors which can be used according to the invention, all mixers and spray equipment which are customarily suitable for this purpose can be employed.

As a result of the use of one or more N-alkyl-lactams of the formula (I) in aqueous spray liquors based on active compounds of the formulae (II) to (IX), the crystallization of active compound both in the concentrated commercial formulation and during application of the aqueous spray liquors prepared from this is either completely suppressed or on the whole prevented in the filters and outlet openings of the spray equipment such that the application of the spray liquors is not impaired.

The preparation and the crystallization behavior of the spray liquors which can be used according to the invention are illustrated by the following examples.

PREPARATION EXAMPLES

EXAMPLE 1

For the preparation of a formulation 13.0 parts by weight of 1-(2-chlorophenyl)-2-(1-chlorocycloprop-1-yl)-3-(1,2,4-triazol 1-yl)-propan-2-ol of the formula

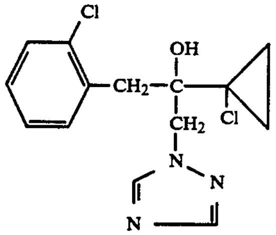

(II)

40.0 parts by weight of N-(n-dodecyl)-caprolactam, 4.0 parts by weight of the emulsifier of the average composition of the formula

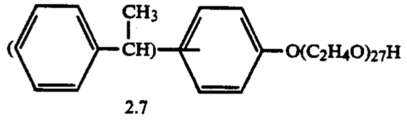

4.0 parts by weight of 4-(n-dodecyl)-phenylsulphonic acid (2-hydroxyethyl)-ammonium salt 4.0 parts by weight of the emulsifier of the average composition of the formula

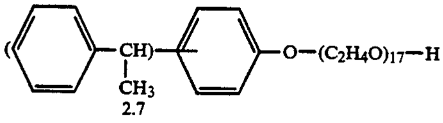

8.0 parts by weight of nonylphenol polyglycol ether having on average 15 oxyethylene units per molecule and 27.0 parts by weight of N-methyl-pyrrolidone are mixed at room temperature and stirred to give a homogeneous liquid. By mixing with water, a spray liquor is prepared from the concentrate thus obtained in which the concentrate is present in a concentration of 1% by weight.

EXAMPLE 2

For the preparation of a formulation 13.0 parts by weight of 1-(2-chlorophenyl)-2-(1-chloro-cycloprop-1-yl)-3-(1,2,4-triazol-1-yl)-propan-2-ol of the formula

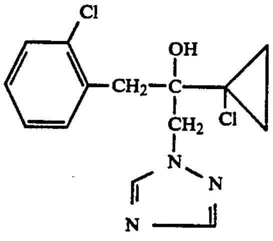

(II)

40.0 parts by weight of N-(n-octyl)-pyrrolidone, 10.0 parts by weight of di-butyl adipate, 4.0 parts by weight of the emulsifier of the average composition of the formula

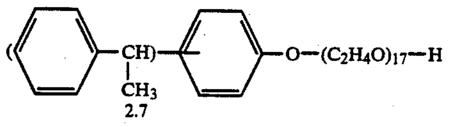

8.0 parts by weight of nonylphenol polyglycol ether having on average 15 oxyethylene units per molecule, 4.0 parts by weight of the emulsifier of the average composition of the formula

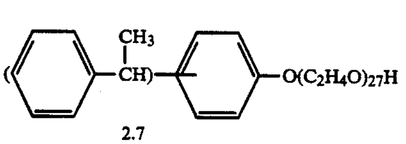

4.0 parts by weight of 4-(n-dodecyl)-phenylsulphonic acid (2-hydroxyethyl)-ammonium salt and 17.0 parts by weight of N-methyl-pyrrolidone, are mixed at room temperature and stirred to give a homogeneous liquid. By mixing with water, a spray liquor is prepared from the concentrate thus obtained in which the concentrate is present in a concentration of 1% by weight.

COMPARISON EXAMPLE A

For the preparation of a formulation 13.0 parts by weight of 1-(2-chlorophenyl)-2-(1-chloro-cycloprop-1-yl)-3-(1,2,4-triazol -1-yl)-propan-2-ol of the formula (II)

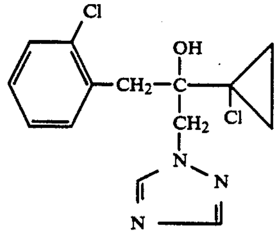

4.0 parts by weight of the emulsifier of the average composition of the formula

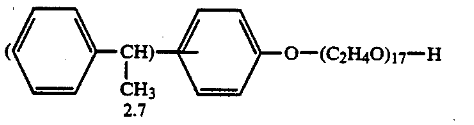

8.0 parts by weight of nonylphenol polyglycol ether having on average 15 oxyethylene units per molecule, 4.0 parts by weight of the emulsifier of the average composition of the formula

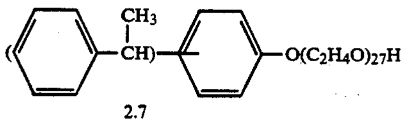

4.0 parts by weight of 4-(n-dodecyl)-phenylsulphonic acid (2-hydroxyethyl)-ammonium salt and 67.0 parts by weight of N-methyl-pyrrolidone, are mixed at room temperature and stirred to give a homogeneous liquid. By mixing with water, a spray liquor is prepared from the concentrate thus obtained in which the concentrate is present in a concentration of 1% by weight.

USE EXAMPLE 1

To test the crystallization properties, 250 ml of an aqueous spray liquor which has a concentrate content of 1% by weight are in each case recirculated through a fine mesh sieve for 15 minutes with the aid of a pump in a flow-through apparatus. After repeating this process eight times with 250 ml of freshly employed spray liquor each time, the crystal deposition on the sieve is photographed.

Figure 2:
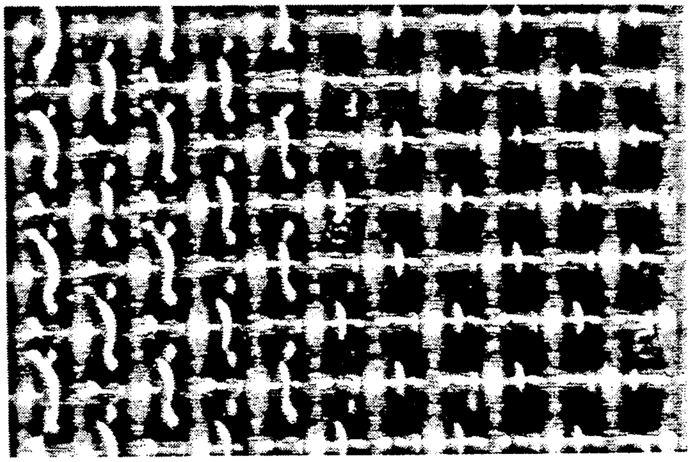
FIG. 2 shows crystal retardation by a caprolactam
Figure 3:
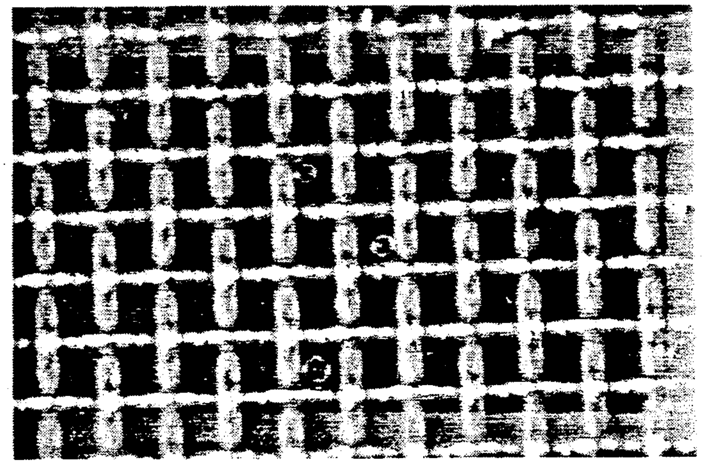
FIG. 3 shows crystal retardation by an octyl pyrrolidone

The corresponding photographs are illustrated in FIGS. 1 to 3 (FIG. 1 to 3).

FIG. 1 shows in an enlargement of 25 times the crystal deposition which results on the sieve on pumping through eight 250 ml batches of the spray liquor containing no crystallization inhibitor, according to Example (A).

FIG. 2 shows in an enlargement of 25 times the crystal deposition which results on the sieve on pumping through eight 250 ml batches of the spray liquor containing N-(n-dodecyl)-caprolactam according to Example (1).

FIG. 3 shows in an enlargement of 25 times the crystal deposition which results on the sieve on pumping through eight 250 ml batches of the spray liquor containing N-(n-octyl)-pyrrolidone according to Example (2), From the Figures, it is visible that the sieve in the case of the known spray liquor according to Example (A) is partially blocked, while in the case of the spray liquors according to Examples (1) and (2) no crystal deposition is observed.

It will be understood that the specification and examples are illustrative but not limitative of the present invention and that other embodiments within the spirit and scope of the invention will suggest themselves to those skilled in the art.

We claim:

1. A sprayable retarded-crystallizing composition comprising water and, by weight, 13 parts of A) 1-(2-chlorophenyl)-2-(1-chloro-cycloprop-1-yl)-3-(1,2,4-triazol-1-yl)-propan-2-ol of the formula

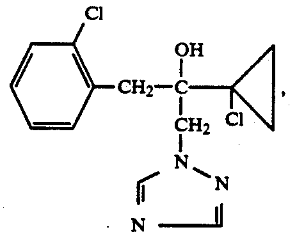

B) about 40 parts of N-(n-dodecyl)-caprolactam or N-(n-octyl)-pyrrolidone,

C) about 4 parts of emulsifier of the average composition of the formula

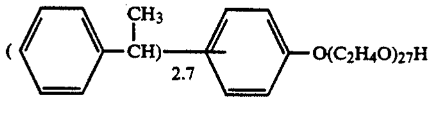

D) about 4 parts of emulsifier of the average composition of the formula

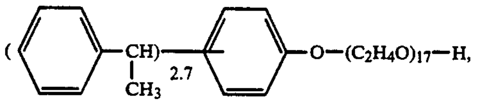

E) about 4 parts of 4-(n-dodecyl)-phenylsulphonic acid (2-hydroxyethyl)-ammonium salt or 10 parts of di-butyl adipate, F) 8 parts of nonylphenol polyglycol ether having an average of 15 oxyethylene units per molecule and G) 17 to 27 parts of N-methyl-pyrrolidone.

2. In the spraying of an aqueous liquor containing the fungicide 1-(2-chlorophenyl)-2-(1-chloro-cycloprop-1-yl)-3-(1,2,4-triazol-1-yl) -propan-2-ol of the formula

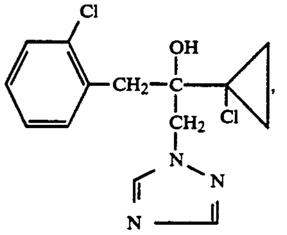

the improvement wherein the aqueous liquor comprises water and, by weight 13 parts of A) 1-(2-chlorophenyl)-2-(1-chloro-cycloprop-1-yl)-3-(1,2,4-triazol-1-yl)-propan-2-ol of the formula

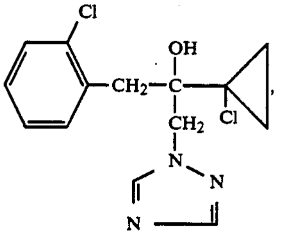

B) about 40 parts of N-(n-dodecyl)-caprolactam or N-(n-octyl)-pyrrolidone,

C) about 4 parts of emulsifier of the average composition of the formula

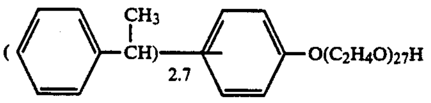

D) about 4 parts of emulsifier of the average composition of the formula

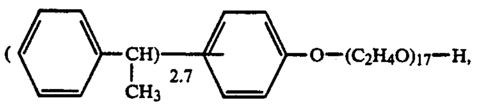

E) about 4 parts of 4-(n-dodecyl)-phenylsulphonic acid (2-hydroxyethyl)-ammonium salt or 10 parts of di-butyl adipate, F) 8 parts of nonylphenol polyglycol ether having an average of 15 oxyethylene units per molecule and G) 17 to 27 parts of N-methyl-pyrrolidone.

3. A sprayable retarded-crystallizing composition comprising water, an emulsifier, an N-alkyl lactam of the formula

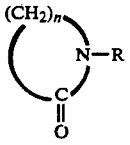

(I)

in which

R represents alkyl having 6 to 18 carbon atoms and n represents the numbers 3, 4 or 5, and at least one fungicide selected from the group consisting of A) 1-(2-chlorophenyl)-2-(1-chloro-cycloprop-1-yl)-3-(1,2,4-triazol-1-yl)propan-2-ol of the formula

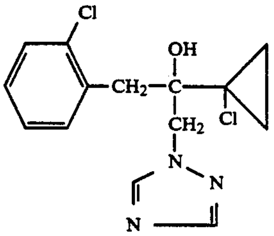

(II)

1-(4-fluorophenyl)-1-(2-fluorophenyl)-2-(1,2,4-triazol-1-yl)ethan-1-ol of the formula

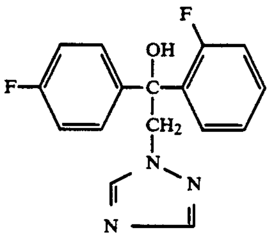

(III)

1-(1,2,4-triazol-1-yl)-2-(2,4-dichlorophenyl)-hexan-2-ol of the formula

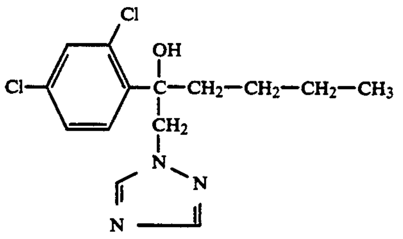

(IV)

1-[bis-(4-fluorophenyl)-methyl-silyl]-1H-(1,2,4- triazole) of the formula

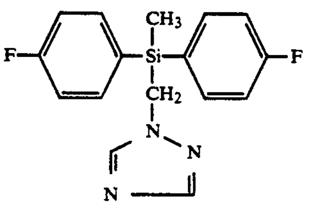

(V)

1-(4-chlorophenyl)-2-(1,2,4-triazol-1-yl)-4,4-dimethyl-pent-1-en-3-ol of the formula

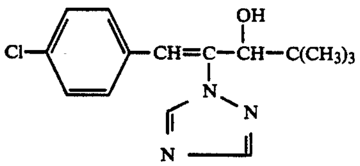
(VI)

1-(2,4-dichlorophenyl)-2-(1,2,4-triazol-1-yl)-4,4-dimethyl-pent-1-en-3-ol of the formula

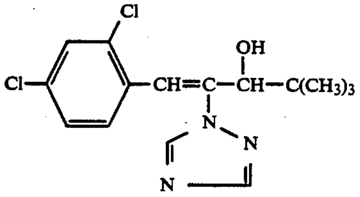
(VII)

1-(4-chlorophenyl)-1-(1-cyclopropyl-ethyl)-2-(1,2,4-triazol-1-yl)-ethan-1-ol of the formula

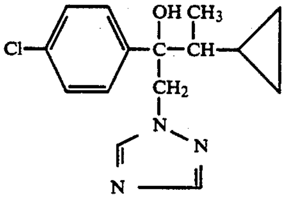
(VIII)

and 1-(4-chlorophenyl)-3-phenyl-3-cyano-4-(1,2,4-triazol-1-yl)-butane of the formula

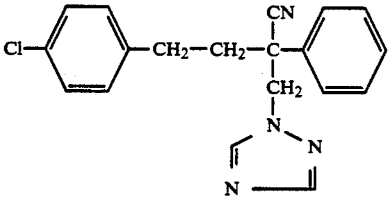
(IX)

the fungicide being present in from 0.0001 to 3% by weight and the weight ratio of active compound to N-alkyl lactam ranging from 1:0.2 to 1:6.

4. A composition according to claim 3, wherein the N-alkyl lactam is N-(n-dodecyl)-caprolactam.

5. A composition according to claim 3, wherein the N-alkyl lactam is N-(n-octyl)-pyrrolidone.

6. A composition according to claim 3, wherein the N-alkyl lactam is N-(n-dodecyl)-pyrrolidone.

7. A composition according to claim 3, wherein the N-alkyl lactam is a mixture of N-(n-octyl)-pyrrolidone and N-(n-dodecyl)-pyrrolidone.

8. In the spraying through a nozzle of a dilute aqueous liquor containing an emulsifier and 0.0001 to 3% by weight of at least one fungicide selected from the group consisting of A) 1-(2-chlorophenyl)-2-(1-chloro-cycloprop-1-yl)-3-(1,2,4-triazol-1-yl)-propan-2-ol of the formula

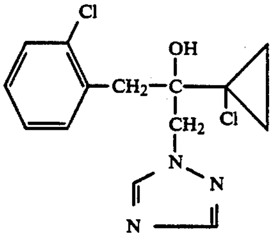
(II)

1-(4-fluorophenyl)-1-(2-fluorophenyl)-2-(1,2,4-triazol-1-yl)-ethan-1-ol of the formula

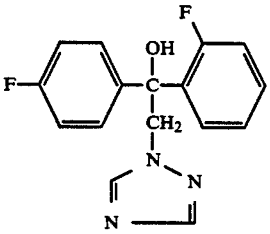
(III)

1-(1,2,4-triazol-1-yl)-2-(2,4-dichlorophenyl)-hexan-2-ol of the formula

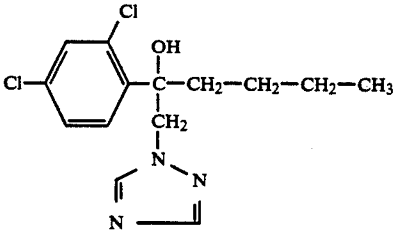
(IV)

1-[bis-(4-fluorophenyl)-methyl-silyl]-1H-(1,2,4-triazole) of the formula

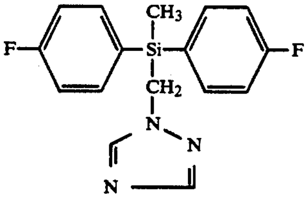
(V)

1-(4-chlorophenyl)-2-(1,2,4-triazol-1-yl)-4,4-dimethyl-pent-1-en-3-ol of the formula

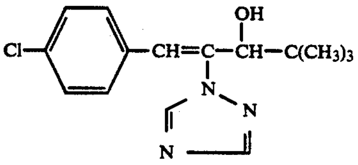
(VI)

1-(2,4-dichlorophenyl)-2-(1,2,4-triazol-1-yl)-4,4-dimethyl-pent-1-en-3-ol of the formula

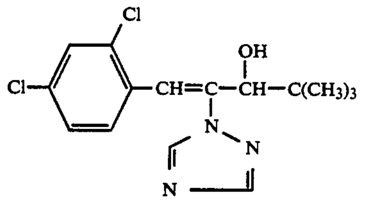

(VII)

1-(4-chlorophenyl)-1-(1-cyclopropyl-ethyl)-2-(1,2,4-triazol-1-yl)ethan-1-ol of the formula

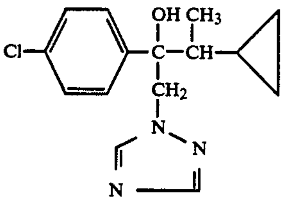

(VIII)

and 1-(4-chlorophenyl)-3-phenyl-3-cyano-4-(1,2,4-triazol-1-yl)-butane of the formula

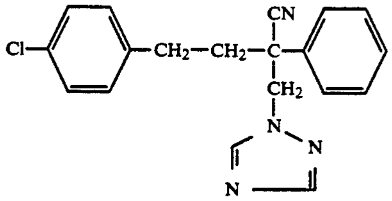

(IX)

the improvement which comprises including in the liquor an N-alkyl-lactam of the formula

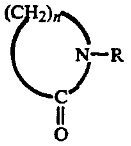

(I)

in which

R represents alkyl having 6 to 18 carbon atoms and n represents the numbers 3, 4 or 5, the weight ratio of active compound to N-alkyl lactam ranging from 1:0.2 to 1:6, whereby crystallization of the fungicide on the spraying nozzle is inhibited.

* * * * *